US012262699B2

(12) United States Patent
Massaro et al.

(10) Patent No.: US 12,262,699 B2
(45) Date of Patent: Apr. 1, 2025

(54) INSECT RELEASE DEVICES

(71) Applicant: Verily Life Sciences LLC, South San Francisco, CA (US)

(72) Inventors: Peter Massaro, San Carlos, CA (US); Robert Sobecki, Brisbane, CA (US); Charles Behling, Brisbane, CA (US); Brian Wasson, Columbus, OH (US)

(*) Notice: Subject to any disclaimer, the term of this patent is extended or adjusted under 35 U.S.C. 154(b) by 208 days.

(21) Appl. No.: 16/189,286

(22) Filed: Nov. 13, 2018

(65) Prior Publication Data

US 2019/0141969 A1 May 16, 2019

Related U.S. Application Data

(60) Provisional application No. 62/587,125, filed on Nov. 16, 2017.

(51) Int. Cl.
*A01K 67/033* (2006.01)
*B64D 1/08* (2006.01)
(Continued)

(52) U.S. Cl.
CPC .............. *A01K 67/033* (2013.01); *B64D 1/08* (2013.01); *F41A 19/55* (2013.01); *F42B 12/46* (2013.01);
(Continued)

(58) Field of Classification Search
CPC .......... A01K 67/033; B64D 1/08; B64D 1/16; B64U 2101/69
(Continued)

(56) References Cited

U.S. PATENT DOCUMENTS 2,160,436 A 5/1939 Jones
3,047,259 A * 7/1962 Tatnall .................... F42B 10/50
244/158.9
(Continued)

FOREIGN PATENT DOCUMENTS

CN 104890883 9/2015
CN 106114863 11/2016
(Continued)

OTHER PUBLICATIONS

Mubarqui et al., "The smart aerial release machine, a universal system for applying the sterile insect technique", PloS One vol. 9,7 e103077. Jul. 18, 2014, doi:10.1371/journal.pone.0103077.
(Continued)

*Primary Examiner* — Christopher D Hutchens
(74) *Attorney, Agent, or Firm* — Kilpatrick Townsend & Stockton LLP

(57) ABSTRACT

One example insect release device includes a vessel defining a volume, the vessel has first and second surfaces substantially opposite each other, the first surface defining an opening into the volume; a population of insect larvae or pupae or adult insects within the volume; and a seal positioned to obstruct the opening and adhered to the first surface. Another example insect release device includes a vessel defining a volume; a population of insect larvae or pupae or adult insects disposed within the volume; wherein the vessel is permanently sealed, and wherein release of the insect larvae or pupae or adult insects occurs upon rupture of the vessel. A further example insect release device includes a vessel defining a volume; a population of insects disposed within the volume; and a gimbal mechanism coupled to the vessel, the gimbal configured to maintain a substantially constant orientation of the vessel.

20 Claims, 13 Drawing Sheets

(51) Int. Cl.
    *F41A 19/55*     (2006.01)
    *F42B 12/46*     (2006.01)
    *F42B 12/56*     (2006.01)
    *F42B 12/76*     (2006.01)
    *F42B 12/36*     (2006.01)
    *F42B 25/00*     (2006.01)

(52) U.S. Cl.
    CPC .............. *F42B 12/56* (2013.01); *F42B 12/76* (2013.01); *F42B 12/367* (2013.01); *F42B 25/00* (2013.01)

(58) Field of Classification Search
    USPC .................................. 206/251, 521; 244/113
    See application file for complete search history.

(56) References Cited

U.S. PATENT DOCUMENTS

| | | | | |
|---|---|---|---|---|
| 3,123,117 | A * | 3/1964 | Nourse et al. | B64D 1/02 206/521 |
| 4,106,438 | A | 8/1978 | Nelson | |
| 4,368,690 | A | 1/1983 | Tenzer | |
| 4,498,420 | A | 2/1985 | Botterman et al. | |
| 4,825,577 | A | 5/1989 | Brannon | |
| 5,113,799 | A * | 5/1992 | Carr | A01K 67/033 119/6.5 |
| 6,511,016 | B2 * | 1/2003 | Bar | F42B 10/50 244/113 |
| 6,516,565 | B1 * | 2/2003 | Fima | A01G 9/0293 47/84 |
| 6,561,125 | B1 | 5/2003 | Lohsomboon | |
| 6,626,313 | B2 * | 9/2003 | Herbstreit | A01K 67/033 220/4.25 |
| 6,712,317 | B1 * | 3/2004 | Warren | B64D 1/08 244/138 R |
| 9,314,010 | B2 * | 4/2016 | Moreto | A01K 67/033 |
| 9,505,496 | B2 * | 11/2016 | Markov | B64D 1/08 |
| 9,522,747 | B2 * | 12/2016 | Coleman | B64G 1/62 |
| 10,773,803 | B2 * | 9/2020 | Qiu | B64D 1/02 |
| 2006/0266292 | A1 | 11/2006 | Duckworth | |
| 2009/0176303 | A1 * | 7/2009 | Schlesinger | A01K 63/04 435/293.1 |
| 2012/0017834 | A1 | 1/2012 | Holland et al. | |
| 2012/0192508 | A1 * | 8/2012 | Burdine | E02D 5/80 52/155 |
| 2014/0020630 | A1 | 1/2014 | Courtright | |
| 2015/0320024 | A1 | 11/2015 | Loos | |
| 2017/0267344 | A1 | 9/2017 | Lepek et al. | |
| 2017/0267346 | A1 * | 9/2017 | Lepek | B64D 1/16 |
| 2018/0206464 | A1 * | 7/2018 | Massaro | G05D 7/0605 |
| 2018/0265199 | A1 * | 9/2018 | Colosimo | B64U 70/50 |
| 2019/0116719 | A1 * | 4/2019 | Fletcher | B64D 1/16 |
| 2019/0223426 | A1 * | 7/2019 | Macadar Angier | A01M 1/106 |
| 2020/0375162 | A1 * | 12/2020 | Metlitz | A01K 29/00 |
| 2022/0022434 | A1 * | 1/2022 | Yoshioka | A01K 67/033 |

FOREIGN PATENT DOCUMENTS

| | | |
|---|---|---|
| CN | 106973733 | 7/2017 |
| CN | 107249460 | 10/2017 |
| DE | 102009008592 A1 | 8/2010 |
| JP | 2005204604 | 8/2005 |
| JP | 2008289431 | 12/2008 |
| WO | 2017049746 | 3/2017 |
| WO | 2017154004 | 9/2017 |

OTHER PUBLICATIONS

International Application No. PCT/US2018/061009, International Preliminary Report on Patentability, mailed May 28, 2020, 8 pages.
International Application No. PCT/US2018/061009, International Search Report and Written Opinion, mailed Jan. 25, 2019, 9 pages.
European Application No. 18879850.8, Extended European Search Report, mailed Jul. 13, 2021, 7 pages.
Chinese Application No. 201880068536.3 , Office Action, Mailed On Aug. 10, 2021, 9 pages.
Singapore Application No. 11202003569Q , Written Opinion, Mailed On Oct. 11, 2021, 8 pages.
Chinese Application No. 201880068536.3 , Office Action, Mailed On Feb. 16, 2022, 23 pages.
European Application No. 18879850.8 , "Office Action", Aug. 27, 2024, 5 pages.

* cited by examiner

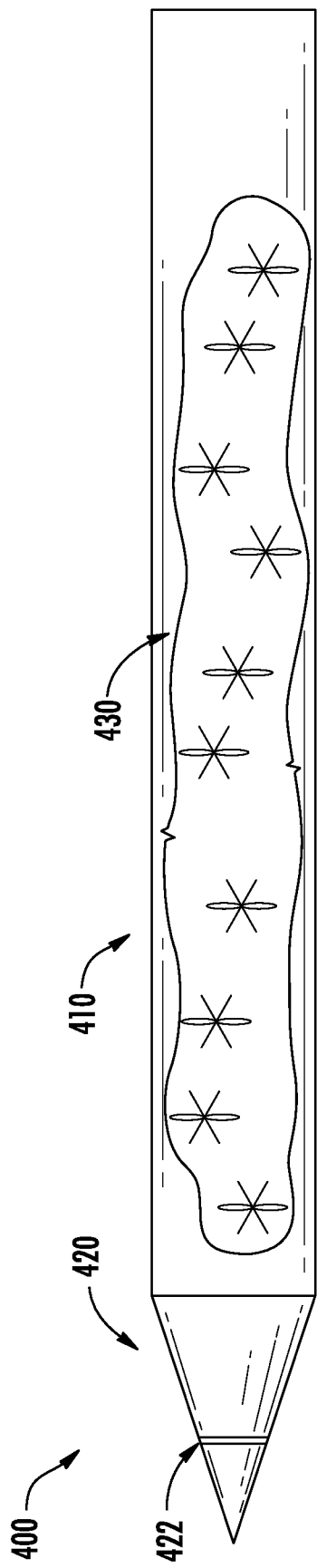
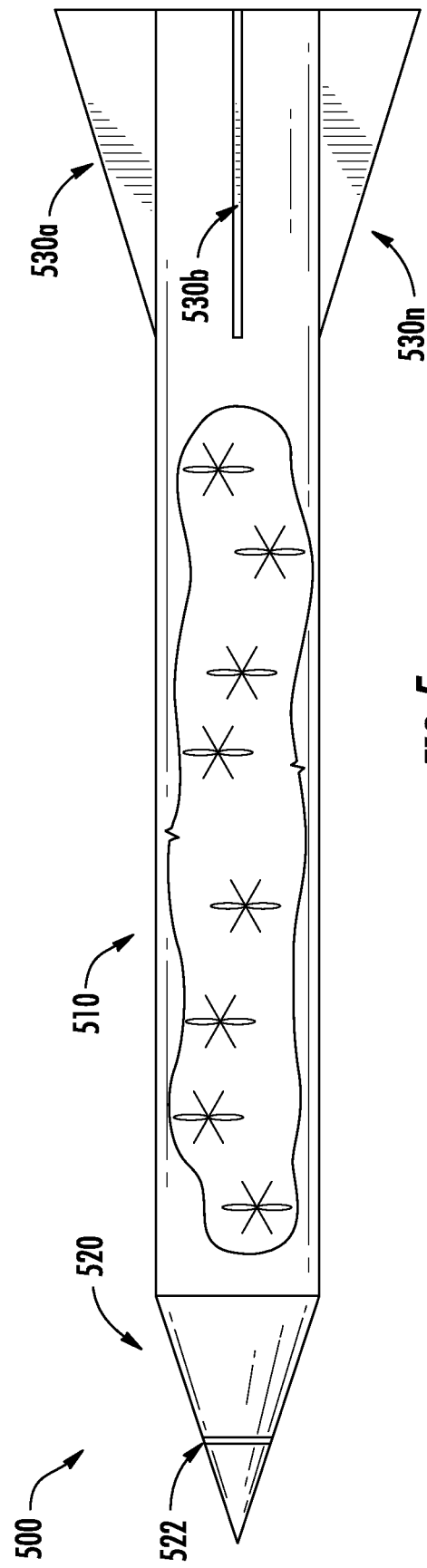

INSECT RELEASE DEVICES

CROSS-REFERENCE TO RELATED APPLICATIONS

This application claims priority to U.S. Provisional Application No. 62/587,125, filed Nov. 16, 2017, entitled "Insect Release Devices," which is hereby incorporated by reference in its entirety herein.

FIELD

The present application generally relates to devices to release insects into an environment.

BACKGROUND

All continents except Antarctica suffer from the plague of mosquito-vectored diseases. Various techniques for the control of mosquito populations involve the generation of sterile male insects for release into the wild for mating with local females. These techniques may employ systems for releasing the reared insects into the wild.

SUMMARY

Various examples are described for insect release devices. One example insect release device includes a vessel defining a volume, the vessel comprises first and second surfaces substantially opposite each other, the first surface defining an opening into the volume; a population of insect larvae or pupae or adult insects disposed within the volume; and a seal positioned to sufficiently obstruct the opening to prevent an adult insect from passing through the opening, the seal adhered to the first surface.

Another example insect release device includes a vessel defining a volume; a population of insect larvae or pupae or adult insects disposed within the volume; wherein the vessel is permanently sealed, and wherein release of the insect larvae or pupae or adult insects occurs upon rupture of the vessel.

A further example insect release system includes an insect release device comprising: a cylindrical tube defining a volume, the cylindrical tube having first and second ends; a population of insect larvae or pupae or adult insects disposed within the volume; a substantially conical end member coupled to and sealing the first end of the cylindrical tube, the substantially conical end member constructed of a material having a first thickness, the substantially conical end member defining a groove running around the edge of an inner or outer surface, the groove creating a second thickness of the material thinner than the first thickness; and an end member coupled to and sealing the second end of the cylindrical tube.

Another example insect release device includes a vessel defining a volume; a population of insects disposed within the volume; and a gimbal mechanism coupled to the vessel, the gimbal configured to maintain a substantially constant orientation of the vessel.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIGS. 4-5 show example insect release devices that may be suitable for a launch system;

DETAILED DESCRIPTION

Figure 1A:
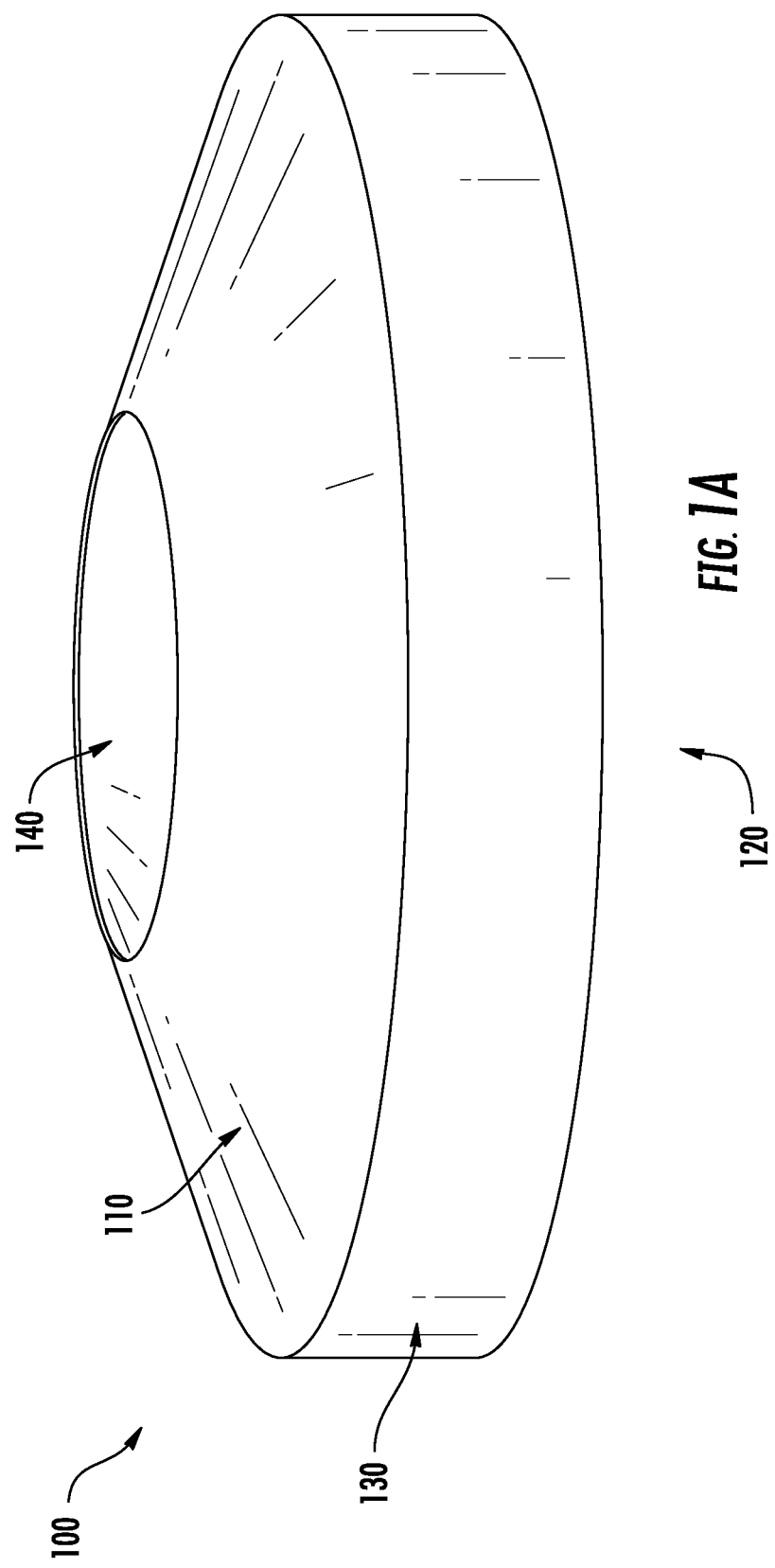
FIGS. 1A-1C show an example insect release device that may be suitable for ground deployment.

Examples are described herein in the context of insect release devices. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

To help eliminate insect-borne diseases, sterile male insects, such as mosquitos, may be released into an environment, where they mate with female insects, but will not generate any offspring. Thus, the insect population is reduced over time. To help effectively control an insect population in such a way, release vehicles, such as cars or trucks, may traverse roads through a geographic region and release thousands of insects in a relatively short time, e.g., a few minutes. Release mechanisms in such environments can be relatively complex as power, weight, and long-term storage of insects may not be issues. For example, insects may be loaded into a release mechanism only a few minutes or hours before they are released into the environment.

In some cases, however, insect release areas may not be easily traversable by a vehicle. For example, hilly, swampy, or overgrown terrain may be desirable locations to release modified insects, but may be impassable to ground vehicles. Thus, other approaches may be employed. For example, release containers may be released from airborne vehicles, such as helicopters, airplanes, or drones, or may be placed by hand. Further, because insect release in such locations may be difficult to achieve from the ground, it may be practically impossible to retrieve any insect release containers after they have released their respective population of insects. Thus, release containers may remain behind in the environment long after their useful life has expired.

Insect release devices according to the present disclosure may be constructed of biodegradable materials that help ensure that the release of insects into an environment does not pollute the environment. In addition, bio-degradable materials may be taken advantage of to enable delayed release of insects from various insect release devices and systems according to this disclosure. For example, rather than filling an insect release device with a population of adult insects, it may instead be populated with insect larvae or pupae, larvae food, and, if appropriate, water or another liquid. Insect larvae or pupae may tolerate higher population densities than adult insects, and thus, a release container may be able to hold a larger number of larvae or pupae than adult insects.

Some example insect release devices may be constructed of biodegradable materials that will begin decaying and ultimately cause one or more ruptures in the insect release device. Thus, as the pupae are maturing within the release device, the release device may degrade and rupture, allowing adult insects that mature from the pupae to escape from the release device and into the environment. Thus, the use of properly constructed biodegradable release devices can serve at least two purposes other than containing and protecting the pupae or insects: (i) it can delay the release of insects, such as until after pupae begin to mature into adult insects, and (ii) it can allow the release device to completely degrade to prevent pollution within the release environment. Further, the example release devices may be used to introduce insect populations into areas that are not easily reachable by a ground vehicle.

These illustrative examples are given to introduce the reader to the general subject matter discussed herein and the disclosure is not limited to this example. The following sections describe various additional non-limiting examples and examples of systems and methods for insect release devices.

Figure 1B:
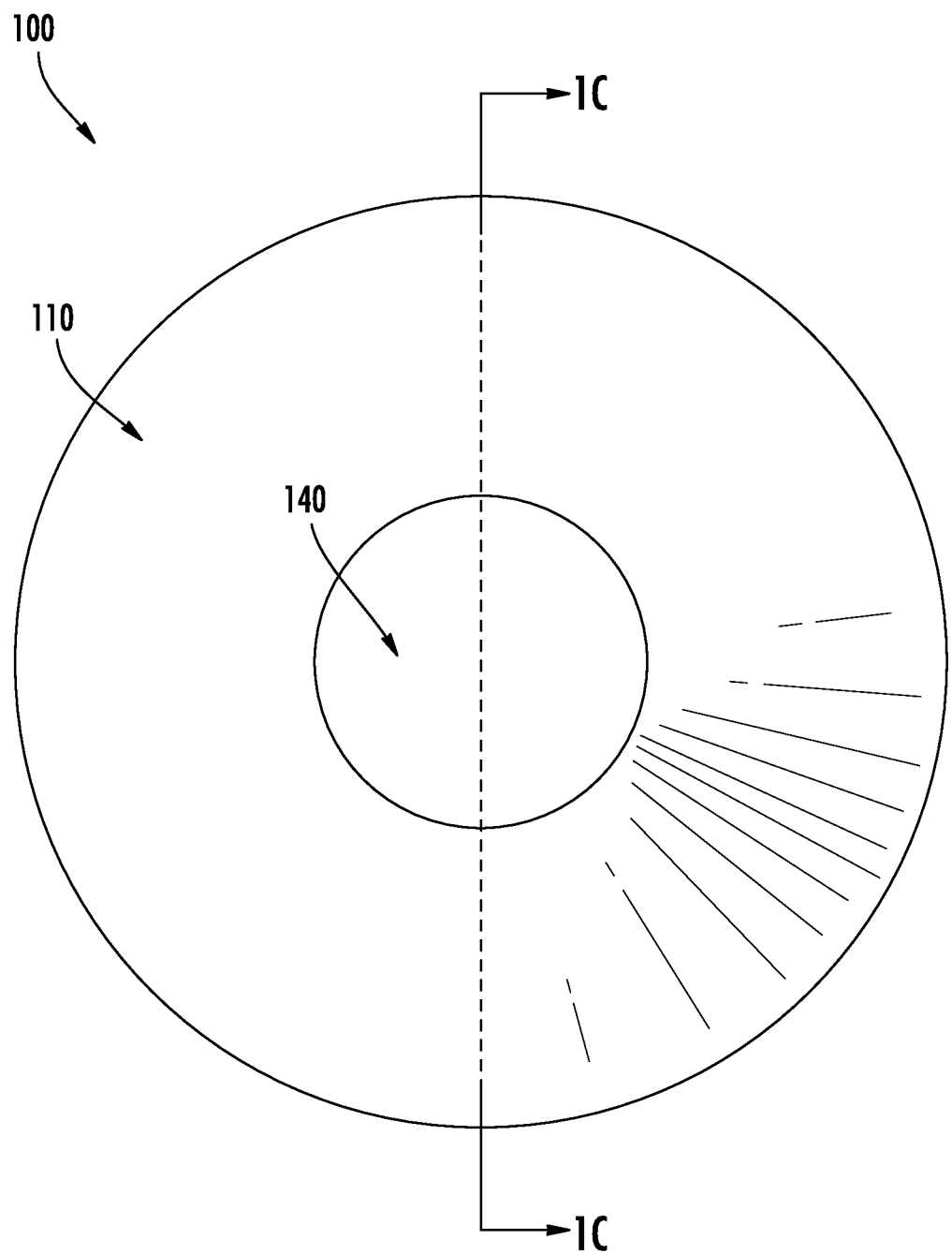
Figure 1C:
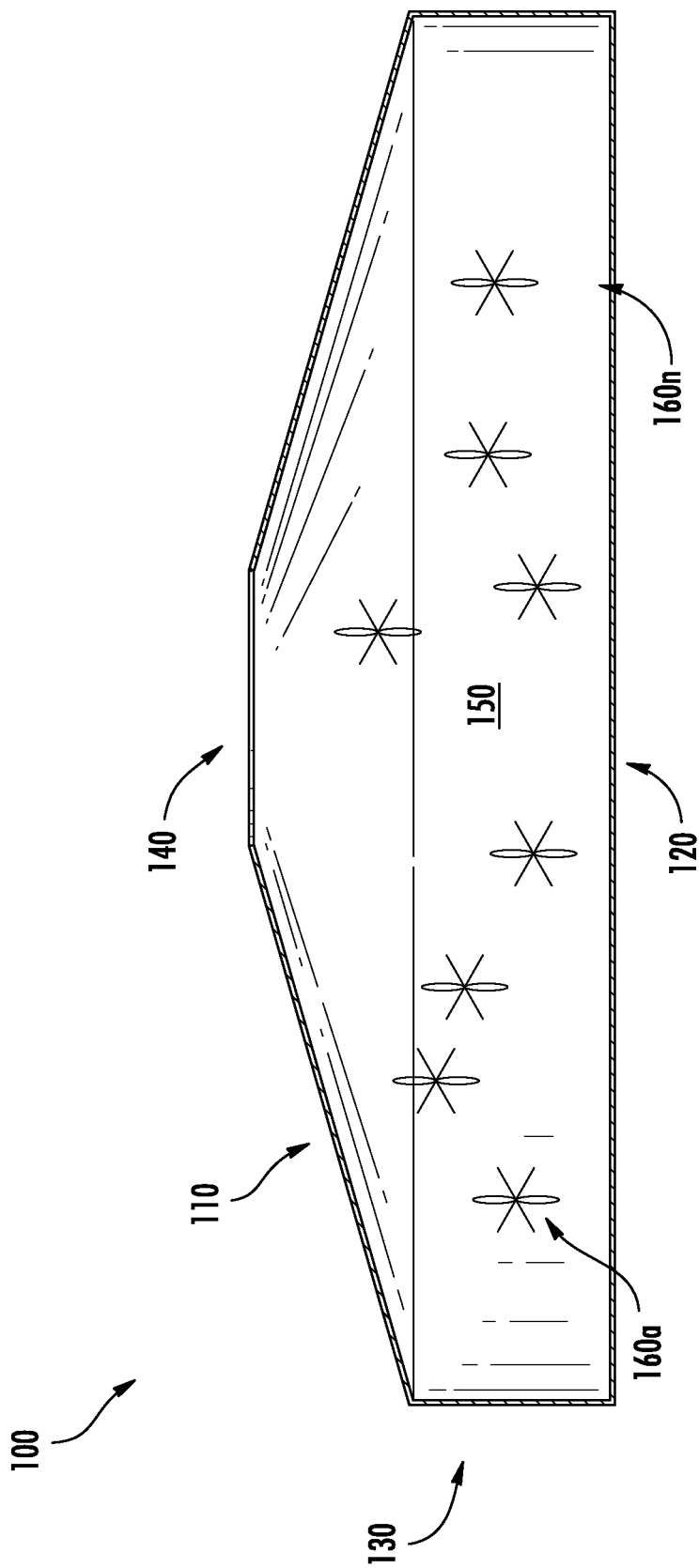

Referring now to FIGS. 1A-1C, FIGS. 1A-1C show an example insect release device 100. This example insect release device 100 includes a vessel that has upper and lower surfaces 110, 120. The lower surface 120 is substantially planar to allow the release device 100 to be set on a surface, such as the ground or a table. The upper surface 110 is angled away from the lower surface 120 and defines an opening 140 through which an insect population may be introduced within the release device 100 and through which they may escape at a later time. By angling the shape of the upper surface 110 away from the lower surface 120, it may help insects within the vessel to escape through the opening 140.

The vessel also has a perimeter wall 130 that couples the upper and lower surfaces 110, 120 together to define a volume 150 within the vessel, shown in FIG. 1C, which shows cross-section A of the release device 100 from FIG. 1B. It is within this volume 150 that an insect population 160*a*-*n* may be stored prior to release ('n' may be any integer value greater than zero). In some examples, adult insects may be placed within the vessel; however, insect larvae or pupae, as well as food or water, or a damp surface that the larvae or pupae may rest upon, may be placed within the vessel instead or in addition.

After a population of adult insects or insect larvae or pupae are placed within the insect release device 100, a seal is placed over the opening 140 and adhered, or otherwise coupled (e.g., stapled, tied, etc.), to the upper surface 110 to prevent the insect population from escaping prior to the insect release device 100 being in position. At a later time, the release device 100 may be positioned at a release location and the seal may be removed. If the insect population is adult insects, they may immediately begin to escape from the release device 100 through the opening 140. Otherwise, they may mature into mature insects and later escape through the opening 420.

In this example, the insect release device 100 is at least partially constructed of a biodegradable material so that it does not need to be retrieved at a later date. Thus, in some examples, a seal positioned across the opening 140 may be left in place and instead, the release device 100 may be allowed to degrade and rupture, thereby allowing insects within it to escape. Such an example may be employed in cases where insect larvae or pupae and water or food are placed within the release device 100. Such an insect population may need additional time to mature into adults prior to release, which may provide time for the release device 100 to degrade and rupture.

The example insect release device 100 shown in FIGS. 1A-1C is substantially 6 inches in diameter, which may be sufficiently large to store several thousand adult insects. Alternatively, a larger number of insect larvae or pupae may be placed in the example release device 100 as they may require less space than an adult insect. In some examples, an example insect release device 100 may have a larger diameter, or may have a different shape than the substantially circular shape of the release device 100 shown in FIGS. 1A-1C. For example, a release device 100 may have a circular, spherical or spheroid, rectangular, square, cubic, or any other suitable shape.

Suitable biodegradable materials for this example insect release device 100, as well as any other example release device according to this disclosure, include cornstarch foam, one or more pectin capsules, paper, mushroom-based foam, or plant-based plastic substitutes.

Figure 2A:
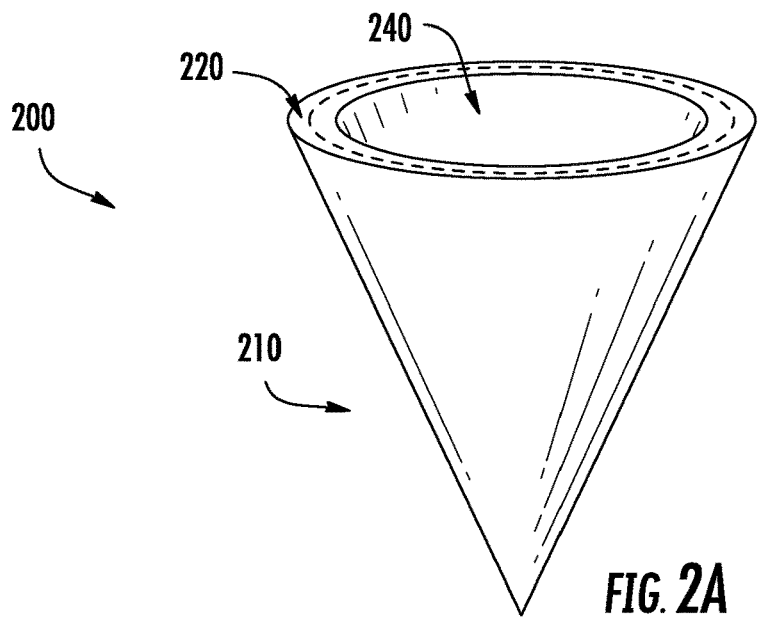
FIGS. 2A-2C show another example insect release device that may be suitable for ground deployment.
Figure 2B:
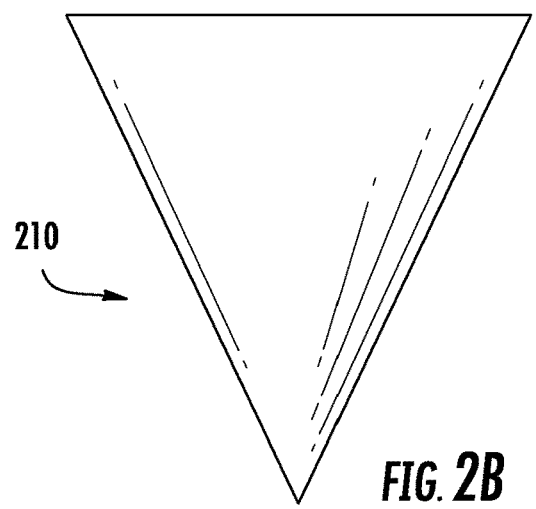
Figure 2C:
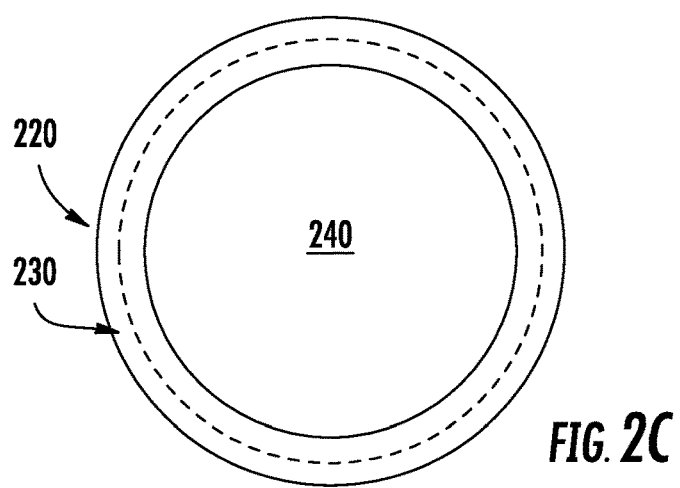

Referring now to FIGS. 2A-2C, FIGS. 2A-2C show another example insect release device 200 that is configured for ground release of insects. The insect release device 200 in FIGS. 2A-2C includes a vessel having a lower surface 210 and an upper surface 220 and defining an interior volume. The lower surface 210 defines a cone that may be pressed into a surface, such as into dirt or grass. The upper surface 220 is planar in this example and defines an opening 240 through which an insect population may be placed within the vessel or escape from the vessel. And while this example employs a planar upper surface 220, any suitable shape may be employed for the upper surface 220.

After an insect population has been placed within the vessel, the vessel may be sealed by placing a seal 230 over the opening 240 and adhering it to the upper surface 220. As with the example shown in FIGS. 1A-1C, the seal 230 may be removed after the insect release device 200 has been placed at a release location.

Alternatively, and similar to the example discussed above with respect to FIGS. 1A-1C, the vessel may be at least partially constructed of any suitable biodegradable material, such as those discussed above. After the insect population has been placed within the vessel, a seal 230 may be adhered to the vessel, such as by adhering it to the upper surface 220. The insect release device 200 may then be positioned at a release location and allowed to degrade and rupture to allow the insect population to escape the release device 200, rather than removing the seal.

As with the example discussed above with respect to FIGS. 1A-1C, the insect population may be either (or both) adult insects or insect larvae or pupae. In addition to the insect population, water or food may also be placed within the release container to feed the insect population prior to its release, or a damp surface that the larvae or pupae may rest upon may be positioned within the release container.

Figure 3A:
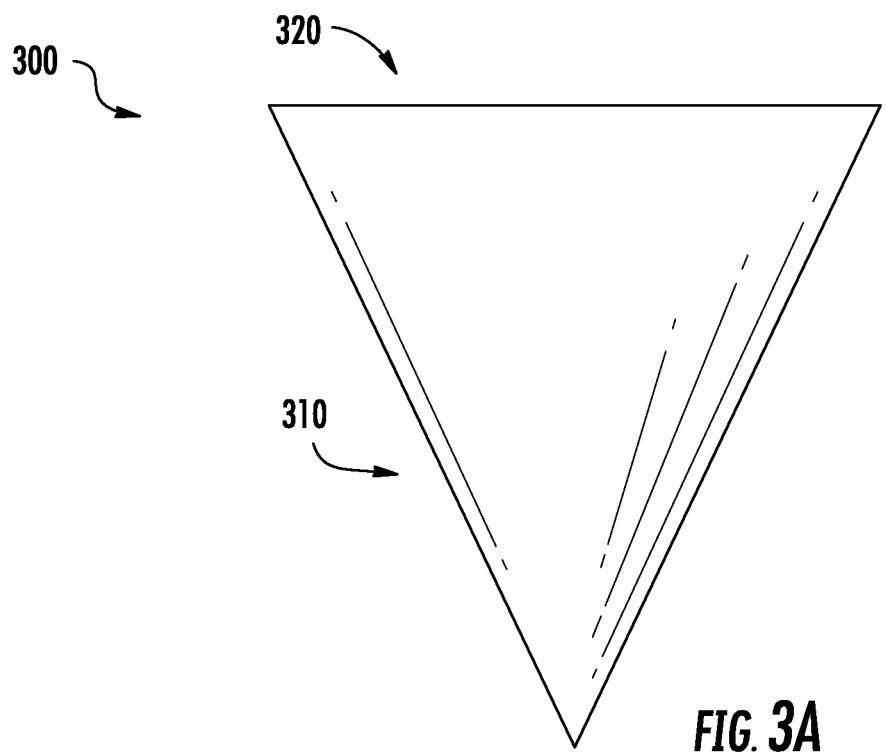
FIGS. 3A-3C show another example insect release device that may be suitable for aerial deployment.
Figure 3B:
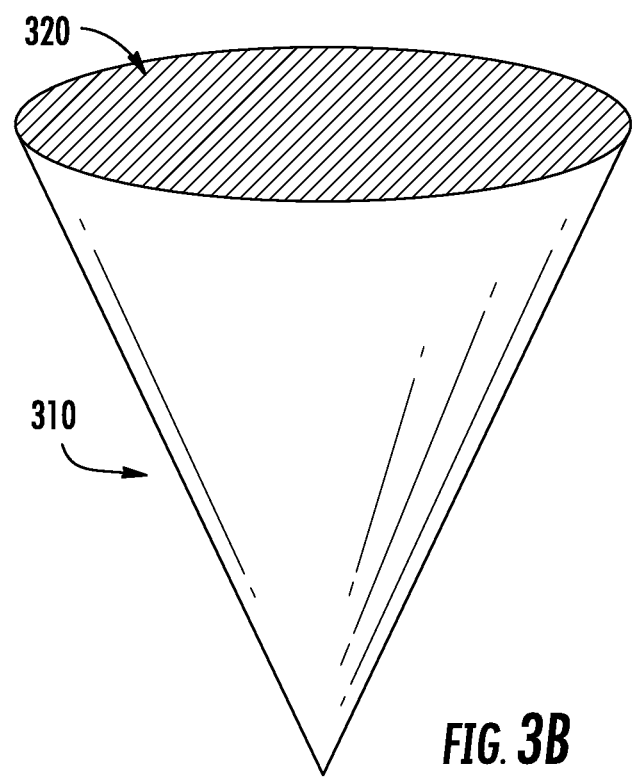
Figure 3C:
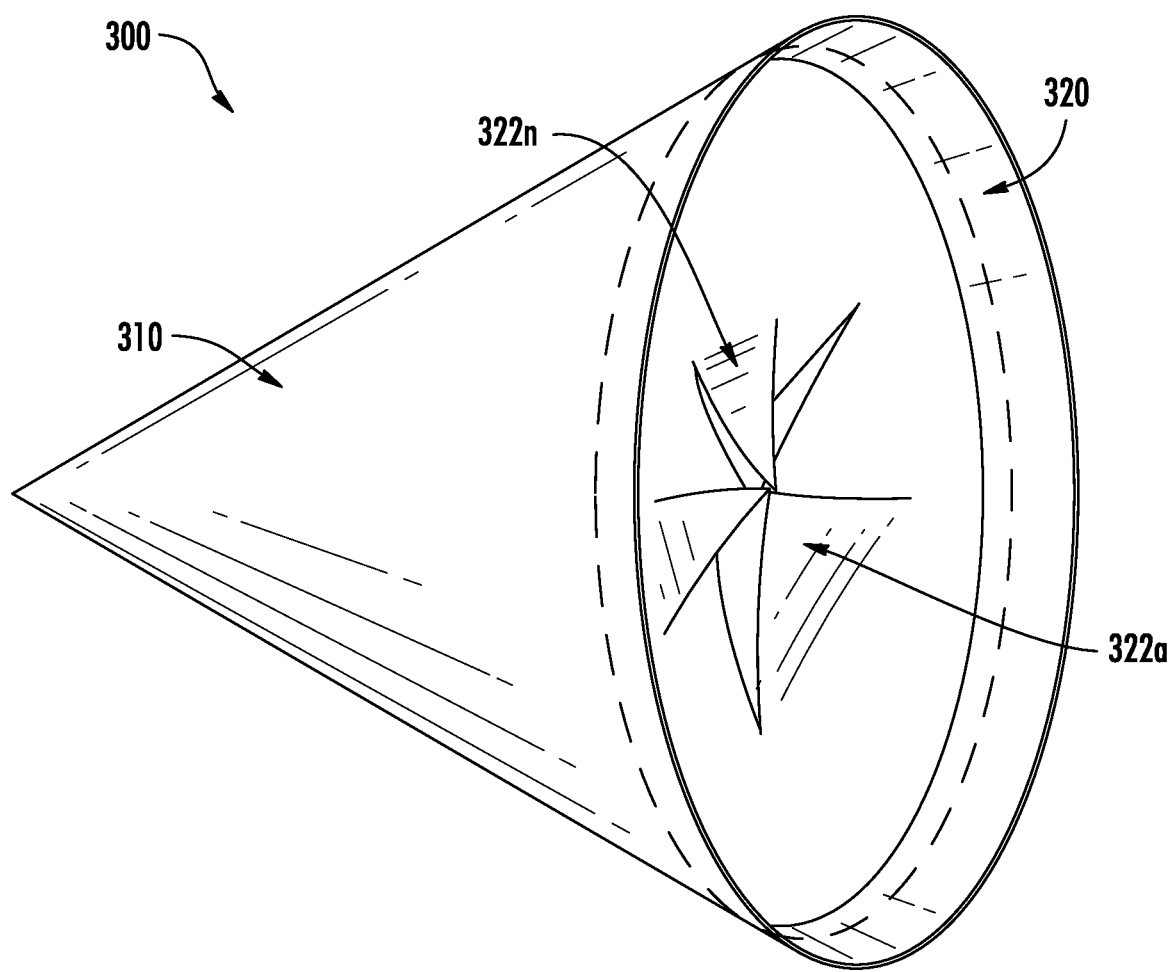
Figure 6:
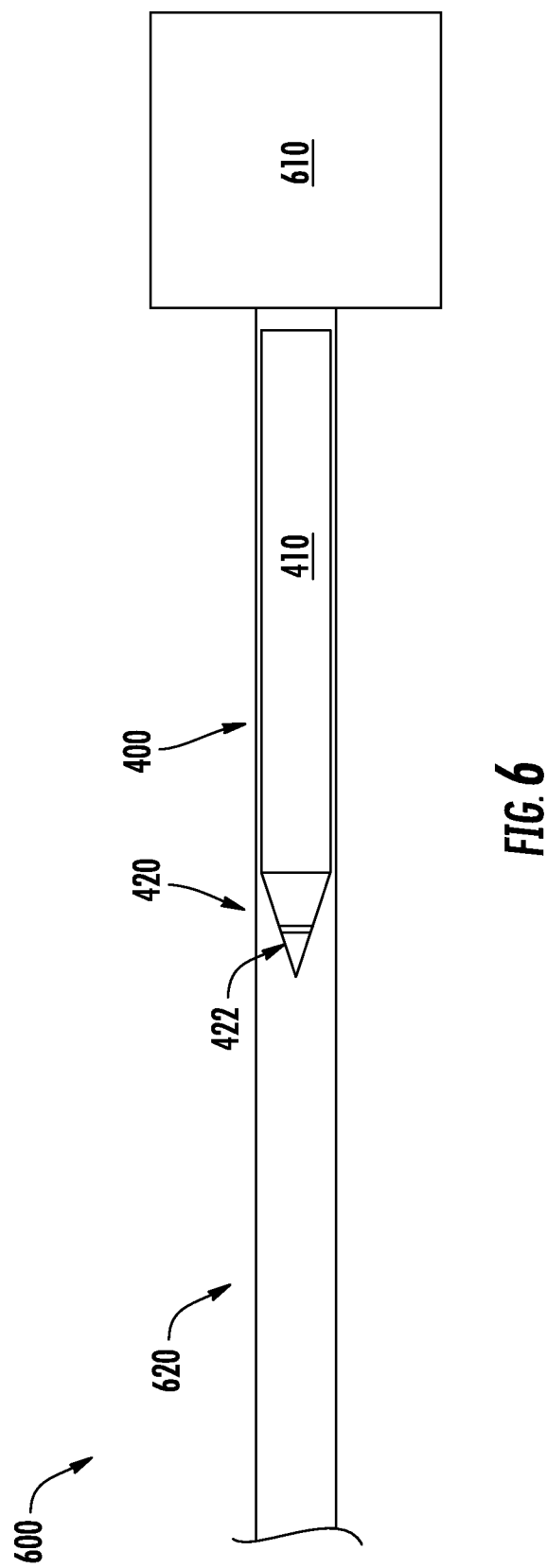
FIG. 6 shows an example insect release system including a launch system.
Figure 7:
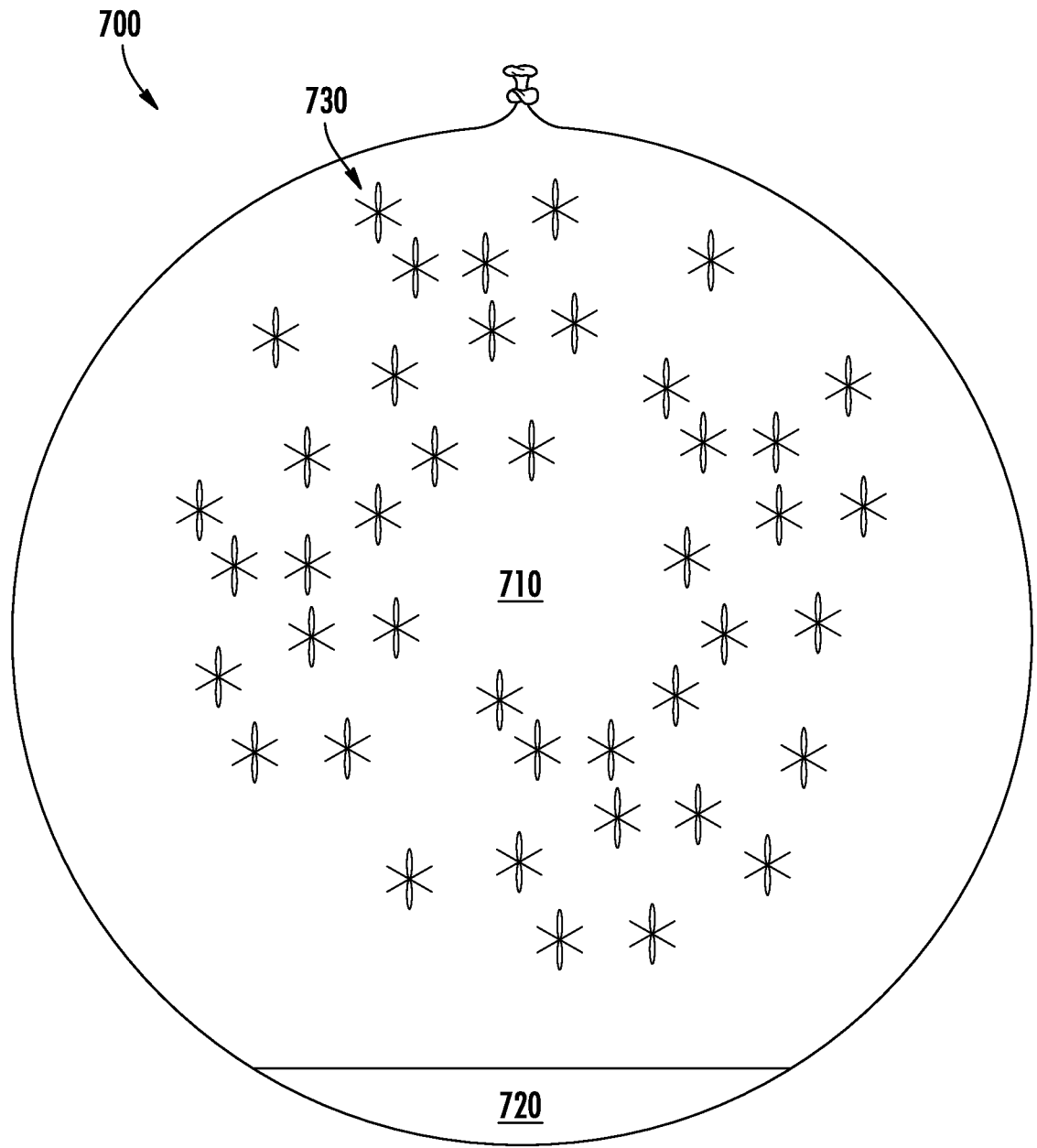
FIG. 7 shows another example insect release device that may be suitable for aerial deployment.

Referring now to FIGS. 3A-3C, FIGS. 3A-3C show an example insect release device 300. This example insect release device 300 includes a vessel having a lower surface 310 that defines a cone and has an upper surface 320 that provides a substantial planar surface. The lower and upper surfaces 310, 320 define a volume in which a population of insects—adult insects, insect larvae or pupae, or both—may be stored prior to release. In some examples, water or food may also be placed within the volume, or a damp surface that the larvae or pupae may rest upon may be positioned within the release container.

In this example, the upper surface 320 is defined from multiple tabs or folds 322a-n ('n' being any integer greater than zero) that can be bent or folded to create the substantially planar surface. The upper surface 320 is coupled to the lower surface 310 by a polyvinyl alcohol ("PVA") thread that dissolves in water. However, any other coupling technique may be used, including adhesives (including water soluble adhesives), staples, etc. The use of PVA thread in this example may allow the thread to dissolve after the insect release devices 300 has been placed in an environment, thereby allowing the upper and lower surfaces 320, 310 to decouple and rupture to allow the insect population to escape from the release device 300. Similarly, the use of a water soluble adhesive may allow for the same decoupling and release of the insects.

Prior to placing an insect population within the volume, the tabs or folds are oriented to allow access to the volume via an opening. After the insects are placed within the volume, the tabs or folds may be bent or folded to establish the substantially planar surface to seal the opening. The tabs or folks may then be coupled to each other to seal the opening. For example, the tabs or folds 322a-n may be sealed with an adhesive, a staple, a thread, etc.

As with the examples shown in FIGS. 1A-1C and 2A-2C, the insect release device 300 may be constructed from a biodegradable material. In this example, the upper and lower surfaces 320, 310 are constructed from paper, however, any other suitable biodegradable material, such as those discussed above, may be used.

The example insect release device 300 shown in FIGS. 3A-3C is designed to allow for airborne release. Thus, it is constructed from a lightweight material, such as paper in this example. The cone shape of the lower surface 310 may help ensure that, after being released from an airborne vehicle (e.g., a drone or manned aircraft), the release device 300 will descend with the tip of the cone oriented towards the ground, thereby exposing the upper surface 320 and water soluble PVA thread to the environment to allow it to degrade and decouple from the lower surface and allow the insect population to escape from the release device 300.

Referring now to FIG. 4, FIG. 4 shows an example insect release device 400. The release device 400 in this example includes a hollow tube 410 and a hollow nose cone 420, which together substantially define a projectile. The hollow tube 410 defines a volume and is sealed at an end opposite the nose cone 420 and open at the other end. An insect population 430 is placed in the hollow tube 410 and the nose cone 420 is fitted and coupled to the end of the hollow tube 410.

As can be seen in FIG. 4, the nose cone 420 defines a groove 422 that runs around a perimeter of the nose cone. The groove 422 creates a region in the nose cone 420 where the nose cone material is thinner than the remainder of the nose cone 420. Thus, a force applied to the nose cone 420 may rupture the nose cone 420 at or near the groove 422, thereby exposing the interior volume of the nose cone 420 and the hollow tube 410 to the environment to allow the insect population 430 to escape.

To facilitate rupture of the nose cone 420, it may be constructed from a biodegradable material, such as those discussed above, and the wall of the nose cone 420 may be construed to be only a few millimeters ("mm") thick, e.g. 2-3 mm or less. The groove 422 may be formed to provide a region with a thinner wall that is, in some examples, 1-2 mm thick. Thus, after the insect release device is fired into an environment (as will be discussed in more detail with respect to FIG. 6), the nose cone 420 may rupture at or near the groove 422 from impacting an obstacle. Or, if it does not rupture the nose cone 420, the groove 422 may biodegrade relatively quickly after it has come to rest in an environment, thereby rupturing the nose cone 420 and ultimately falling away from the release device 400 to allow the insect population to escape.

FIG. 5 shows another example of an insect release device 500 in the shape of a projectile. Similar to the example shown in FIG. 4, the insect release device 500 has a hollow tube 510 and a hollow nose cone 520 with a groove 522. In addition, the example release device 500 includes multiple fins 530a-n ('n' is any positive integer greater than zero) that may help stabilize the insect release device 500 while in flight. The fins 530a-n in this example have a triangular shape, but may have any suitable shape, such as square or rectangular, semicircular, etc. in other examples.

Referring now to FIG. 6, FIG. 6 shows an example system 600 to deliver an insect release device, such as the example release devices 400, 500 shown in FIGS. 4 and 5. The system 600 includes a launch system having a launch tube 620 and a pressurized air source 610. In this example, an example insect release device 400 according to FIG. 4 is positioned within the launch tube 620.

In this example, the pressurized air source 610 is a blower, however, in other examples, the pressurized air source 610 may be a cartridge having a compressed gas, such as carbon dioxide. In some examples, the pressurized air source 610 may be a combustion chamber in which a propellant, such as an aerosol propellant, can be ignited to generate increased air pressure. Still further examples may be employed to generate a volume of increased gas pressure behind the insect release device 400.

The pressurized air source 610 generates gas pressure behind the insect release device 410, propelling it through the launch tube 620 and into the environment. Such a system 600 may be employed to deliver an insect release device into a release location that is otherwise difficult or impractical to enter or reach on foot or with a ground vehicle. Further, based on the speed of the insect release device 400 at impact in the environment, the nose cone 420 may be more likely to rupture as discussed above. Thus, by firing the insect release device 400 from the launch tube 620 at significant speeds, e.g., greater than 25 miles per hour, it may impact in the environment at sufficient speed to rupture the nose cone 420, e.g., at the groove 422.

Referring now to FIG. 7, FIG. 7 shows an example insect release device 700 that may be suitable for airborne release of the release device 700. In this example, the insect release device 700 is an inflated balloon constructed from a stretchable and substantially impermeable material, such as a latex or rubber material. An insect population 730 has been placed within the volume 710 defined by the inflated balloon. In some examples, water or food 720 may also by placed within the volume 710, or a damp surface that the larvae or pupae may rest upon may be positioned within the release container.

After the balloon has been inflated and the insect population has been placed within the balloon, the balloon is sealed, such as by tying shut the opening used to inflate the balloon. The balloon may then be released from an aircraft in an environment, where it can drift to the ground and rupture, thereby releasing the insect population into the environment.

In some example, the insect population 730 may include insect larvae or pupae that are placed into the balloon after it has been partially inflated, along with food and water. The balloon may be fully inflated and sealed and the insect larvae or pupae may be allowed to mature into adult insects prior to the balloon being released into an environment. Such a technique may allow for easier introduction of an insect population into the balloon than forcing adult insects into the balloon. In addition, a greater number of insect larvae or pupae may be inserted using such a technique, thereby allowing a larger population of adult insects to be released into an environment.

Figure 8A:
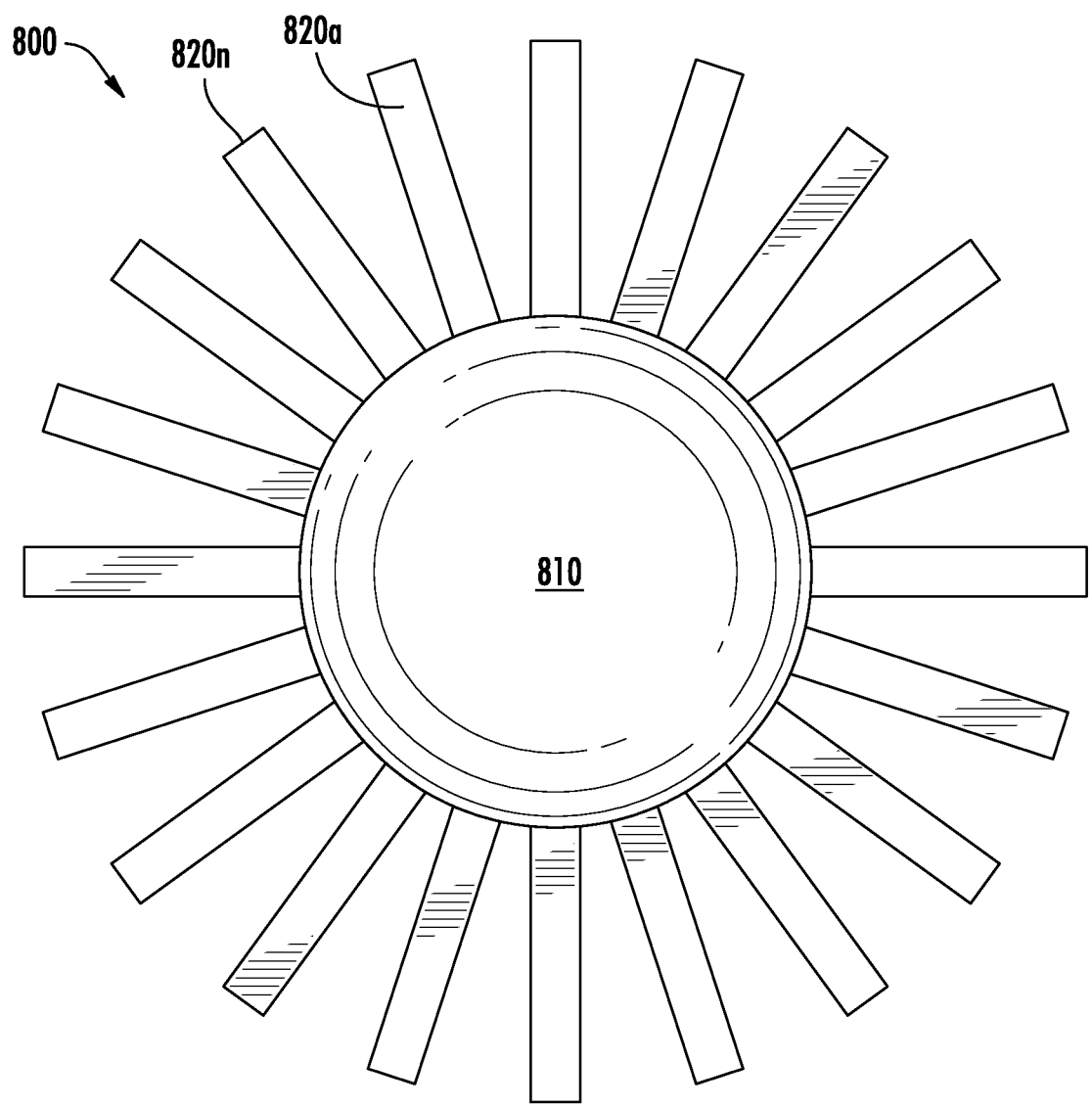
FIGS. 8A-8B show another example insect release device that may be suitable for aerial deployment.
Figure 8B:
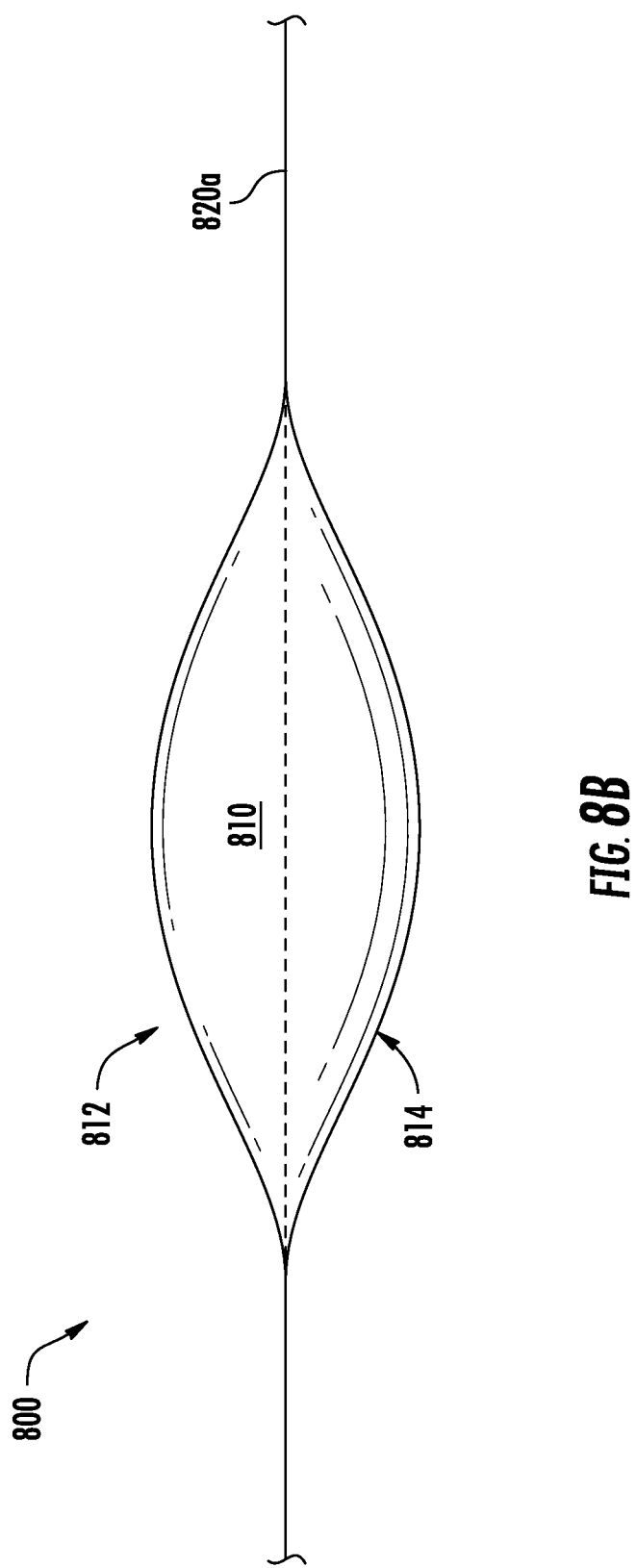

Referring now to FIGS. 8A-8B, FIGS. 8A-8B show an example insect release device 800. This example includes a vessel 810 has upper and lower surfaces 812-814 (shown in FIG. 8B) that define a volume in which a population of insects may be placed, as well as other materials, such as food or water, or a damp surface that the larvae or pupae may rest upon may be positioned within the vessel. A number of fins 820a-n ('n' being any suitable positive integer) extend from the perimeter of the vessel 810 to create a "sunburst"-type cross-section shown in FIG. 8A. The fins 820a-n in this example are generally rectangular and flat. Thus, in the perspective shown in FIG. 8A, the fins' rectangular shape is shown, while in FIG. 8B, their thickness is shown. And while in this example, the fins 820a-n are depicted with a rectangular shape, any suitable shape or arrangement of fins 820a-n may be employed. Further, while the vessel 810 is depicted in this example as having a circular perimeter, in some examples, the vessel 810 may have any suitable perimeter shape, including circular, ovoid, rectangular, square, etc.

In this example, the vessel 810 and fins 820a-n are constructed of a biodegradable paper material, though any suitable biodegradable material as discussed above. The fins 820a-n are attached to the perimeter of the vessel 810 using an adhesive in this example, though in some examples other coupling mechanisms may be employed, including staples, threads, etc. The fins 820a-n are constructed to be flexible and to allow the ends of the fins 820a-n to deflect away from a rest position. Thus, if the insect release device 810 is dropped from a height, the fins 820a-n may provide aerodynamic drag and may flex to help stabilize the release device 800 during its descent.

In some examples, the fins 820a-n and part of the vessel 810 may be formed from the same continuous sheet of material. For example, a substantially circular piece of material may be formed to create an upper surface 812 or lower surface 814 of the vessel 810, and the fins may be formed from the same piece of material, such as by cutting away pieces of material to form the fins 820a-n. A population of insects, as well as other materials in some examples, may be disposed within the vessel 810 before the upper and lower surface 812, 814 are coupled to each other. In some examples, the upper and lower surfaces 812, 814 may be coupled together, such as using an adhesive, staples, tied with a string, etc.

In some examples, a part of the vessel 810 (e.g., the upper or lower surfaces 812, 814) and the fins 820a-n may be cast as a single piece using a mold, such as from a biodegradable plastic material. In some examples, a single mold may be used to cast half of a vessel 810, e.g., an upper surface, as well as fins around half of the perimeter. Two substantially identical parts may be cast from the same mold and coupled together to provide a complete vessel as well as a complete set fins running the full perimeter of the vessel, each half contributing half of the fins.

The insect release device 800 may be suitable for aerial release, such as from a drone, helicopter, plane, or other aircraft. As discussed above, the fins 820a-n may slow the descent of the release device 800 while also preventing the release device 800 from tumbling during its descent. For example, the release device 800 may employ the fins to maintain the upper surface 812 oriented away from the ground throughout the entire descent until the release device 800 ultimately lands on its lower surface 814. Release of the insect population may occur after the vessel 810 biodegrades over time and ruptures. The time to rupture may be adjusted based on the type and thickness of the biodegradable material selected to form the vessel 810 as well as the maturity of the insect population. For example, insect larvae or pupae at different ages may be employed based on the characteristics of the vessel 810, or the construction of the vessel 810, e.g., the size and thickness of the vessel walls, the length and shape of the fins 820a-n, etc. may be designed based on the expected age of the insect larvae or pupae to be placed within the vessel.

In this example, the insect release device 800 is approximately 18 inches in diameter, including the fins. The vessel is approximately 6 inches in diameter, and each fin is approximately 6 inches in length. In some examples, a different ratio of fin length to vessel diameter or width may be employed. For example, longer fins than a diameter (or width) of the vessel 810 may be employed to provide a slower rate of descent, while shorter fins than the diameter or width of the vessel 810 may be employed to provide a faster rate of descent. Rate of descent, and corresponding expected G-forces upon impact with the ground, may be adjusted based on the physical characteristics of the insect population. Hardier insects may allow for a faster descent, while fragile insects may require a relatively slow descent.

Figure 9:
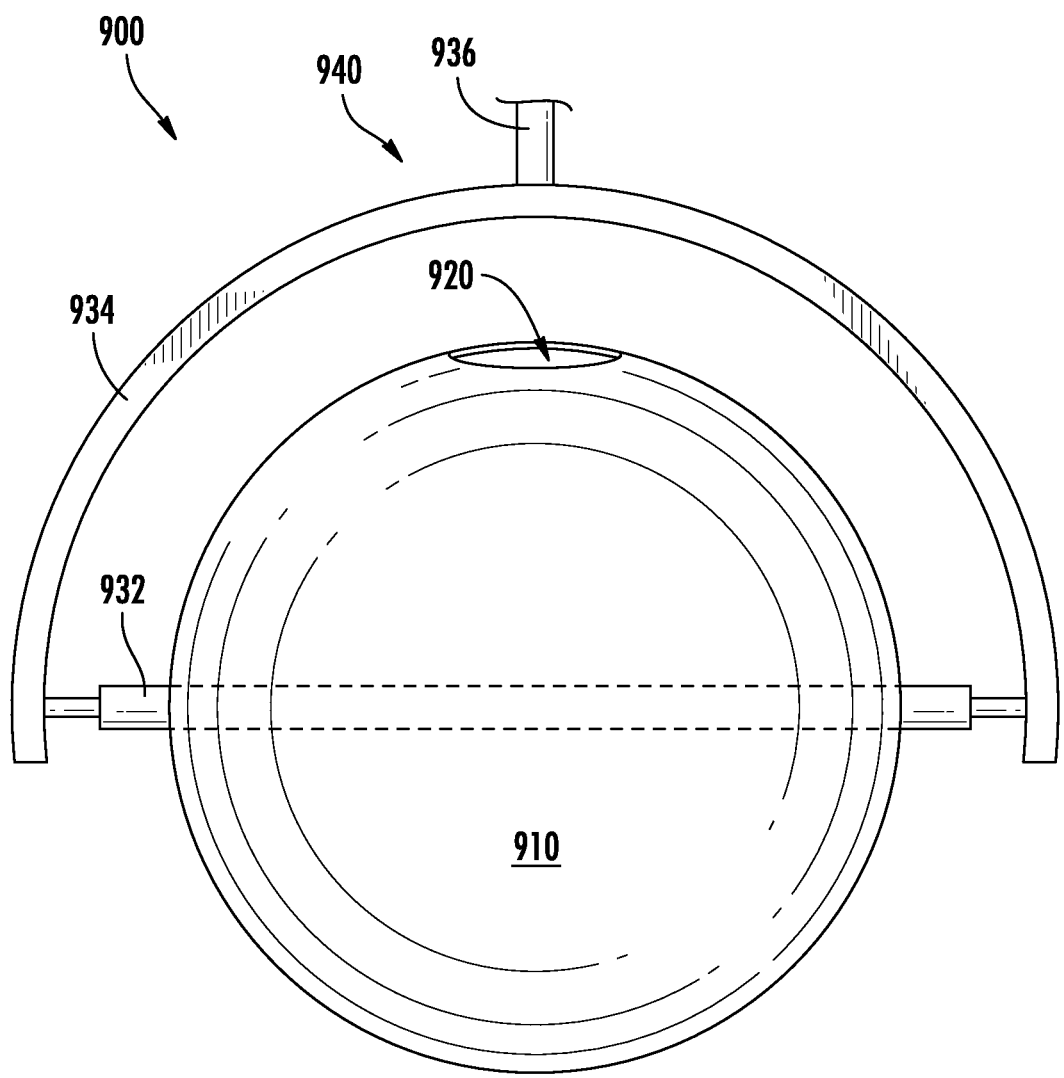
FIG. 9 shows another example insect release device that may be suitable for aerial deployment.

Referring now to FIG. 9, FIG. 9 shows an example insect release device 900 that includes a vessel 910 defining an opening 920. The vessel 910 is coupled to a gimbal mechanism 940. The gimbal mechanism 940 includes provides two members 932 and 934 that provide rotational degrees of freedom (each a "DOF") to the vessel 910. The gimbal mechanism 940 may then be coupled to an external device by the attachment point 936, such as a parachute or a support member, thereby allowing the vessel 910 to maintain a substantially constant orientation, e.g., with the opening 920 oriented away from the ground, even if the parachute or support member moves or changes its orientation. And while this example employs a gimbal mechanism 940 providing two rotational DOFs, other examples may employ gimbal mechanisms providing a greater or lesser number of rotational DOFs.

The vessel 910 in this example has a substantially spherical shape, though in other examples, the vessel 910 may have any suitable shape, including as a cube, a rectangular prism, a cone, a cylinder, etc. The vessel 910 is constructed of a biodegradable material, such as those discussed above. In this example, the vessel 910 defines an opening through which an insect population may be introduced into the vessel 910 or may escape from the vessel 910. For example, the opening 920 may be sealed after an insect population has been introduced into the vessel 910, and at the time of release, the seal may be removed and the release device 910 released into an environment. However, in some examples, the vessel 910 may be permanently sealed, or may be constructed from two pieces and sealed, after an insect population has been introduced into the vessel 910. After release, the vessel 910 may biodegrade and rupture, thereby allowing the insect population to escape into the environment, such as described above with respect to other example insect release devices according to this disclosure.

The gimbal mechanism 940 in this example is configured to provide two rotational DOF to the vessel 910. The first gimbal member 932 is coupled to the vessel 910 and allows rotation about a first axis extending between the coupling points. Thus, the first gimbal member 932 is able to rotate about the first axis without affecting the orientation of the vessel 910. Similarly, the second gimbal member 934 is coupled to the first gimbal member 932 and allows rotation about a second axis from the attachment point 936. The gimbal members 932, 934 have been coupled such that the first and second axes are substantially orthogonal to each other. Thus, the two gimbal members 932, 934 are able to rotate with respect to the vessel 910 while allowing the vessel to substantially maintain an upright orientation, where upright refers to keeping the opening 920 (or the upper surface of the vessel) substantially oriented away from the ground. Thus, as the attachment point 936 moves, e.g., due to movement of a parachute or other member, the gimbal members 932, 934 change their orientation or rotate, thereby maintaining the vessel 910 in a substantially upright orientation.

In some examples the gimbal mechanism 940 may be constructed from a biodegradable material, such as the same biodegradable material as the vessel 910. However, the gimbal mechanism 940 may be constructed from any suitable material or materials.

Figure 10:
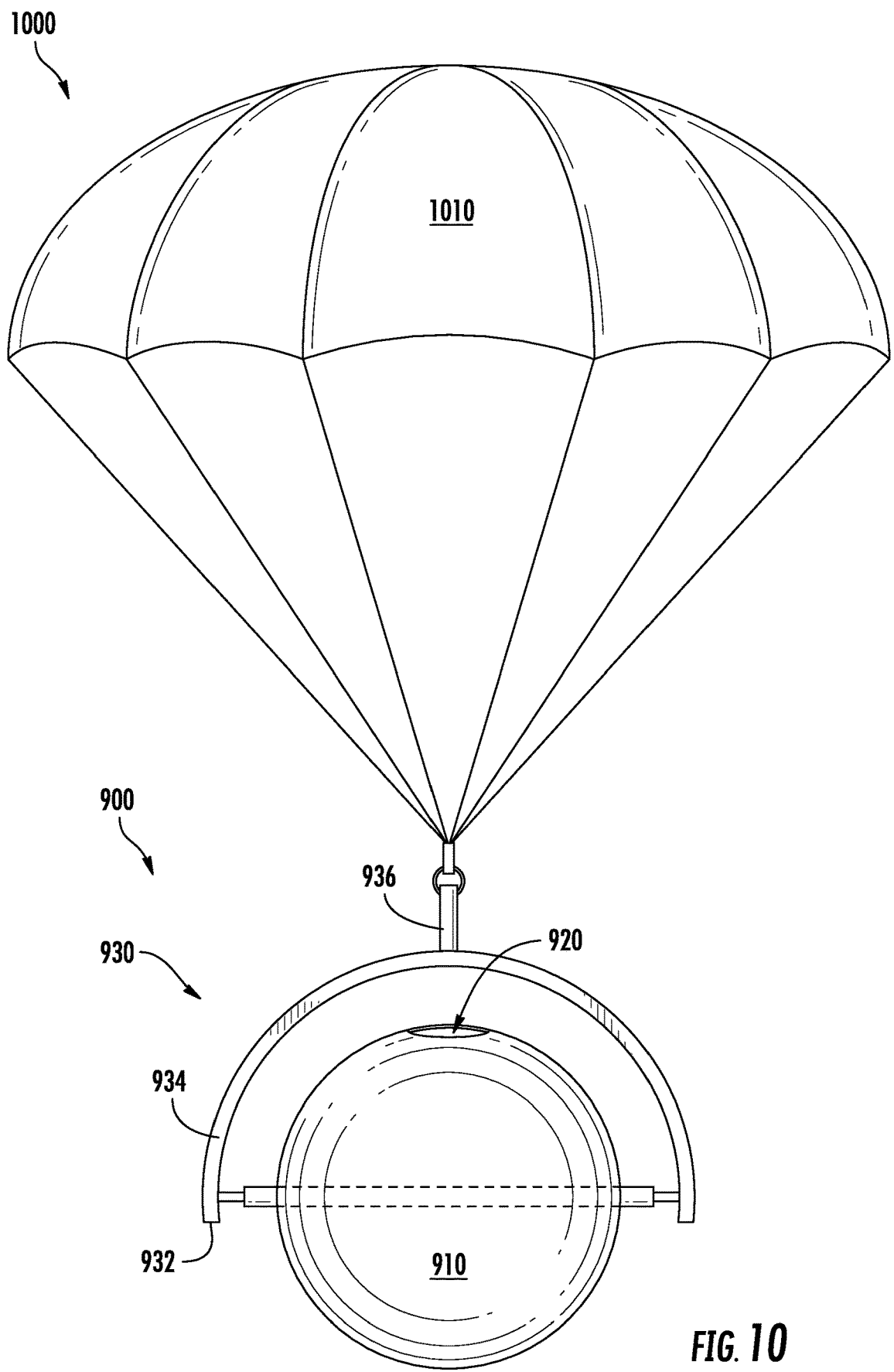
FIG. 10 shows another example insect release system that may be suitable for aerial deployment.

Referring now to FIG. 10, FIG. 10 shows an example insect release system 1000 that includes an example insect release device 900 according to FIG. 9. In this example, the insect release device 900 is directly coupled to a parachute 1010 at the attachment point 936. For example, the attachment point 936 may include a rotatable or pivotable member that is coupled to a hook or eye to which the parachute may be coupled. In some examples, however, the parachute 1010 may be indirectly coupled to the attachment point 936, such as by a cross member or other structure. Thus, after the insect release system 1000 is deployed, the parachute may slow the rate of descent of the system 1000; however, as the parachute is blown about by wind or other turbulence, the gimbal mechanism 940 may allow rotate around the vessel 910, allowing the vessel 910 to maintain its orientation with respect to the ground, such as to maintain the opening 920 oriented away from the ground.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. An insect release device comprising:
   a disc-shaped vessel defining a volume and having a perimeter;
   a plurality of fins extending from the perimeter;
   a population of insect larvae or pupae or adult insects disposed within the volume; and
   wherein the disc-shaped vessel is permanently sealed, and wherein release of the population of insect larvae or pupae or adult insects occurs upon rupture of the disc-shaped vessel.

2. The insect release device of claim 1, wherein water or insect food is disposed within the volume.

3. The insect release device of claim 1, further comprising a damp surface disposed within the volume.

4. The insect release device of claim 1, wherein the disc-shaped vessel comprises a biodegradable material configured to sufficiently decompose within less than substantially 50 hours to rupture the disc-shaped vessel.

5. The insect release device of claim 4, wherein the biodegradable material comprises one or more of (i) a cornstarch foam, (ii) one or more pectin capsules, (iii) paper, (iv) a mushroom-based foam, or (v) a plant-based plastic substitute.

6. The insect release device of claim 1, wherein the plurality of fins are constructed to be flexible and to allow the ends of the fins to deflect away from a rest position.

7. A method of releasing insects into an environment, comprising:
   providing an insect release device comprising:
   a disc-shaped vessel defining a volume and having a perimeter, a plurality of fins extending from the perimeter; and
   a population of insect larvae or pupae or adult insects disposed within the volume, wherein the disc-shaped vessel is permanently sealed, and wherein release of the population of insect larvae or pupae or adult insects occurs upon rupture of the disc-shaped vessel;
   carrying, using a flying vehicle, the insect release device to a release altitude; and
   releasing the insect release device from the flying vehicle.

8. The method of claim 7 wherein water or insect food is disposed within the volume.

9. The method of claim 7, wherein the insect release device further comprises a damp surface disposed within the volume.

10. The method of claim 7, wherein the disc-shaped vessel comprises a biodegradable material configured to sufficiently decompose within less than substantially 50 hours to rupture the disc-shaped vessel.

11. The method of claim 10, wherein the biodegradable material comprises one or more of (i) a cornstarch foam, (ii)

one or more pectin capsules, (iii) paper, (iv) a mushroom-based foam, or (v) a plant-based plastic substitute.

12. The method of claim 7, wherein the plurality of fins are constructed to be flexible and to allow the ends of the fins to deflect away from a rest position.

13. A method of manufacturing an insect release device, comprising:
    forming a first portion of a disc-shaped vessel;
    forming a second portion of the disc-shaped vessel;
    disposing a population of insect larvae or pupae or adult insects disposed on the first portion of the disc-shaped vessel; and
    permanently coupling the first and second portions of the disc-shaped vessel to form the disc-shaped vessel and define a perimeter and a volume containing the population of insect larvae or pupae or adult insects, wherein the disc-shaped vessel comprises a plurality of fins extending from the perimeter.

14. The method of claim 13, further comprising forming the plurality of fins as a part of at least one of the first or second portion of the disc-shaped vessel.

15. The method of claim 13, further comprising forming the plurality of fins, and attaching the plurality of fins to at least one of the first or second portion of the disc-shaped vessel.

16. The method of claim 13 wherein water or insect food is disposed within the volume.

17. The method of claim 13, further comprising disposing a damp surface on the first or second portion of the disc-shaped vessel.

18. The method of claim 13, wherein the disc-shaped vessel comprises a biodegradable material configured to sufficiently decompose within less than substantially 50 hours to rupture the disc-shaped vessel.

19. The method of claim 18, wherein the biodegradable material comprises one or more of (i) a cornstarch foam, (ii) one or more pectin capsules, (iii) paper, (iv) a mushroom-based foam, or (v) a plant-based plastic substitute.

20. The method of claim 13, wherein the plurality of fins are constructed to be flexible and to allow the ends of the fins to deflect away from a rest position.

* * * * *